United States Patent [19]

Venkateshwaran et al.

[11] Patent Number: 5,783,208
[45] Date of Patent: Jul. 21, 1998

[54] TRANSDERMAL DRUG DELIVERY MATRIX FOR COADMINISTERING ESTRADIOL AND ANOTHER STEROID

[75] Inventors: Srinivasan Venkateshwaran; Charles D. Ebert, both of Salt Lake City, Utah

[73] Assignee: TheraTech, Inc., Salt Lake City, Utah

[21] Appl. No.: 683,892

[22] Filed: Jul. 19, 1996

[51] Int. Cl.⁶ .................................................. A61F 13/02
[52] U.S. Cl. ............................................ 424/448; 424/449
[58] Field of Search ..................................... 424/448, 449

[56] References Cited

U.S. PATENT DOCUMENTS

| | | | |
|---|---|---|---|
| 4,482,534 | 11/1984 | Blank | 424/449 |
| 4,537,776 | 8/1985 | Cooper | 514/424 |
| 4,762,851 | 8/1988 | Alexander et al. | 514/420 |
| 4,789,667 | 12/1988 | Makino et al. | 514/424 |
| 4,954,487 | 9/1990 | Cooper et al. | 514/420 |
| 4,986,982 | 1/1991 | Scott | 424/63 |
| 4,994,267 | 2/1991 | Sablotsky | 514/182 |
| 5,023,084 | 6/1991 | Chien et al. | 424/448 |
| 5,296,230 | 3/1994 | Chien et al. | 424/448 |
| 5,460,820 | 10/1995 | Ebert | 424/449 |
| 5,512,292 | 4/1996 | Gale | 424/448 |
| 5,605,702 | 2/1997 | Teillaud | 424/448 |

FOREIGN PATENT DOCUMENTS

| | | |
|---|---|---|
| 0364211 | 4/1990 | European Pat. Off. |
| 60-66759 | 4/1995 | Japan. |
| 60-123417 | 7/1995 | Japan. |

OTHER PUBLICATIONS

Translation of Japanese Laid–Open Patent Publication No. 60–66759, publication date Apr. 16, 1985 entitled "Drug Administration Member".

Translation of Japanese Laid–Open Patent Publication No. 60–123417, publication date Jul. 2, 1985 entitled "Medicinal Preparation".

Primary Examiner—D. Gabrielle Phelan
Attorney, Agent, or Firm—Morrison & Foerster LLP

[57] ABSTRACT

A matrix type transdermal patch for coadministering estradiol and another steroid wherein the matrix is composed of a N-vinyl-2-pyrrolidone-containing acrylic copolymer pressure sensitive adhesive, estradiol, the other steroid, and optionally a permeation enhancer, and the respective fluxes of estradiol and the other steroid from the matrix are independent of the respective concentrations of the other steroid and estradiol in the matrix.

9 Claims, 12 Drawing Sheets

NORMALIZED NEA FLUX AS A FUNCTION OF CONCENTRATION (NO E2)

TRANSDERMAL DRUG DELIVERY MATRIX FOR COADMINISTERING ESTRADIOL AND ANOTHER STEROID

TECHNICAL FIELD

This invention is in the field of transdermal drug delivery. More particularly it relates to a matrix type transdermal patch for coadministering estradiol and another steroid wherein the flux of each steroid from the matrix is independent of the concentration of the other in the matrix.

BACKGROUND

Matrix-type transdermal patches are those in which the drug is contained in and released from a polymer matrix. The matrix is typically made of a pressure sensitive adhesive and defines the basal surface of the patch (i.e. the surface affixed to the skin). While more than one drug may be delivered from such a matrix, the respective fluxes of the individual drugs from the matrix typically depend upon the concentration of the other drug(s) in the pressure sensitive adhesive. This is because the concentration of each drug in the matrix affects the solubility of the other drug(s) in the pressure sensitive adhesive.

EPA 89310350.7 (published 1 Apr. 1990) describes a transdermal matrix type patch for administering estradiol and/or esters of estradiol. The pressure sensitive adhesive component of the patch is a copolymer of 2-ethylhexylacrylate (EHA) and N-vinyl-2-pyrrolidone (NVP). This copolymer is said to provide a means for maintaining a relatively high concentration of estradiol in the matrix without estradiol crystallization. This NVP-containing acrylic copolymer adhesive uses two monomers with very different reactivity ratios, so that for all practical purposes, the polymer is likely to have a "block copolymer" structure, with distinct long chain NVP and EHA domains. Beyond the suggestion that estradiol esters may be used as a drug, this application provides no suggestion or data regarding the inclusion of a second, different steroid in the matrix.

DISCLOSURE OF THE INVENTION

The invention is a transdermal patch for administering estradiol and another steroid comprising:

a) a backing layer; and b) a matrix layer comprising:

(i) a NVP-containing acrylic copolymer pressure sensitive adhesive;

(ii) estradiol; and (iii) another steroid wherein the flux of said other steroid from the matrix layer is independent of the concentration of estradiol in the matrix layer and the flux of estradiol from the matrix layer is independent of the concentration of the other steroid in the matrix layer.

Another aspect of this invention is a method for providing hormone replacement therapy to a woman in need of such therapy comprising applying the above described patch to the skin of said woman.

MODES FOR CARRYING OUT THE INVENTION

Figure 1:
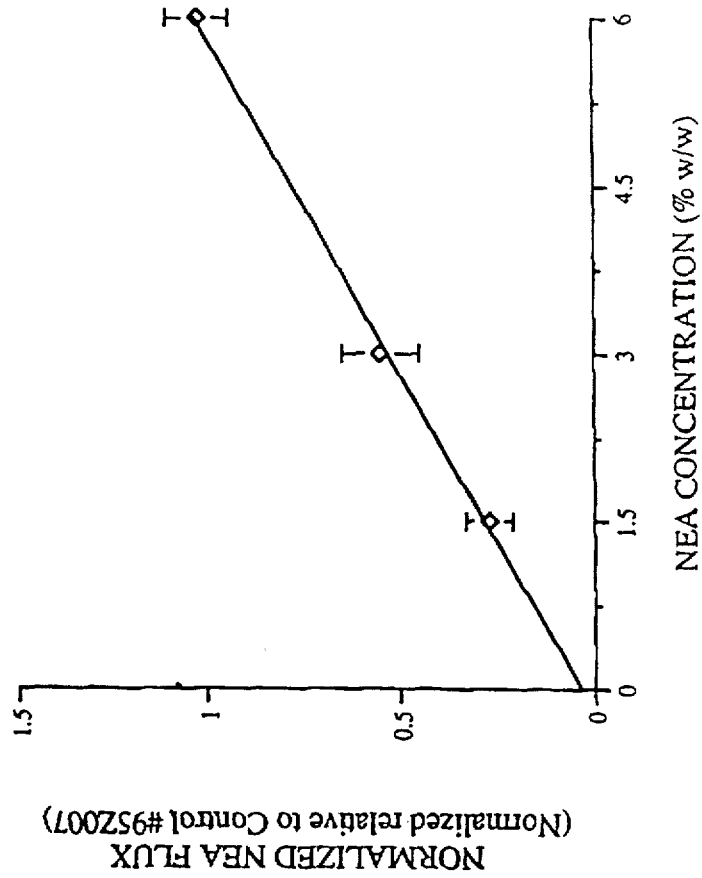
FIG. 1 is a graph showing normalized flux of norethindrone acetate (NEA) as a function of the NEA loading concentration from a NVP-containing matrix. The Y axis shows normalized NEA flux relative to control #95Z007 (y=0.165x+0.035, $r^2$=0.998).

As used herein the term "transdermal" intends percutaneous and transmucosal (e.g. transbuccal) administration, i.e., passage of the drug by diffuision through unbroken skin or mucosa into circulation.

The term "another steroid" intends a steroid other than estradiol or an ester of estradiol. Examples of such other steroids, without limitation, are progesterone, norethindrone acetate, norethindrone, desogestrel, gestodene, norgestrel, levonorgestrel, testosterone, methyltestosterone and androsteinedione.

The term "flux" intends the in vitro rate of release of steroid per unit area as measured using the procedure described in the examples, infra.

The term "independent" intends that the flux of each steroid from the matrix does not vary significantly as the concentration of the other steroid in the matrix varies. Typically the variation in flux, if any, will be in the range of ±35%.

The pressure sensitive adhesive copolymer component of the matrix is a NVP-containing acrylic copolymer. The NVP constitutes 5 to 50 mol % with other acrylic monomers comprising 40 to 95 mol %. Other monomers typically used in acrylic copolymer adhesives are described in the Background section, supra. EPA 89310350.7 for example discloses a copolymer of NVP and EHA. The EHA constitutes 45 to 80 mol %, preferably 55 to 70 mol % of the copolymer whereas NVP constitutes 20 to 55 mol %, preferably 30 to 45 mol % of the copolymer.

Estradiol is present in the matrix at about 1 to 20% by weight, preferably about 2 to 12% by weight of the matrix. The other steroid will normally constitute 1 to 20% by weight of the matrix, depending upon the particular steroid involved. For instance, when the other steroid is norethindrone acetate it will typically constitute 10 to 8% by weight of the matrix and when the other steroid is testosterone, it will typically constitute 1 to 10% by weight of the matrix. Although the precise mechanism by which the flux of estradiol is independent of the concentration of the other steroid in the matrix (and vice versa) is not known, it is possible that the "block copolymer" structure of NVP-containing acrylic copolymers may result in each steroid selectively partitioning into a specific block domain and being released from that domain independent of the other steroid.

In addition to the copolymer and the steroids, the matrix may also contain one or more skin permeation enhancers. Examples of enhancers that may be used, without limitation, include saturated and unsaturated fatty acids and their esters, alcohols, monoglycerides, acetate, diethanolamides and N, N-dimethylamides, such as oleic acid, propyl oleate, isopropyl myristate, glycerol monooleate, glycerol monolaurate, methyl laurate, lauryl alcohol, lauramide diethanolamide and combinations thereof. Saturated and unsaturated sorbitan esters, such as sorbitan monooleate and sorbitan monolaurate may also be used. Other conventional additives used in matrix type patches may also be included in the matrix. Such additives include, without limitation, tackfiers, fillers or other additives that affect the adhesive properties of the matrix and additives such as glycerin, that reduce skin irritation, and additives that affect the solubility of the steroids in the copolymer.

The matrix may be formulated by mixing the adhesive (which is typically obtained in solution), estradiol, other steroid, permeation enhancer (if necessary) and other additives (if desired) in appropriate proportions, casting the mixture onto a substrate (e.g. a release liner), drying the cast layer to remove the solvent, and laminating a backing layer on to the dried polymer matrix. The backing layer will typically be occlusive. Release liner and backing layer materials are well known in the transdermal patch art.

The invention is further illustrated by the following examples. These examples are not intended to limit the invention in any manner.

EXAMPLES

Example 1

(A) Norethindrone Acetate (NEA) only matrices:

Matrix laminates containing norethindrone acetate (NEA, Schering AG, Berlin, Germany) were fabricated as follows. The percent solid adhesive of an EHA/NVP acrylic copolymer adhesive (TSR Adhesive, Sekisui Chemical Co., Japan), was determined by weighing a small amount of adhesive solution in a preweighed aluminum dish. The solvent was evaporated by overnight drying in a convection oven at 70° C., and the dish was reweighed. The percent solids was calculated by dividing the dry weight by the wet weight and multiplying by 100. Known amounts of TSR adhesive solution were weighed into glass bottles. From the weight of the adhesive solution and the percent solid adhesive, the amount of adhesive in the solution was calculated. Appropriate quantities of NEA and sorbitan monooleate permeation enhancer (ARLACEL 80, ICI Americas, Wilmington, Del.) were added to yield various compositions as shown in Table I below (Formulations 1–3), all percentages being calculated on a dry weight basis. Each glass bottle was then tightly capped, sealed with laboratory film (PARAFILM "M", American National Can Company, Greenwich, Conn.), and rotated overnight.

About 8 ml of the drug/sorbitan monooleate/TSR solution was then dispensed on a release liner (siliconized polyester release liner, Release Technologies, Inc., W. Chicago, Ill.), and cast with a 10 mil gap casting knife. This cast mixture was dried in a convection oven at 70° C. for 15 minutes to yield a dry film approximately 2.0 mil thick. A backing film (polyethylene backing film, 3M Corp., St. Paul, Minn.) was then laminated onto the dry adhesive film using a rubber roller. This matrix laminate was used for in vitro skin flux measurements which were performed as described below.

In vitro skin flux studies were conducted using modified Franz diffusion cells. Heat separated human epidermal membrane was cut into rectangular strips. The matrix laminates (described above) were cut into circular punches of 0.71 cm² surface area. After the release liner was peeled and discarded, the circular punches were laminated onto the stratum corneum surface of the epidermal membrane. Each piece of the skin-punched matrix sandwich was loaded between the donor and receiver compartments of a diffusion cell, with the epidermal side facing the receiver compartment, and clamped in place. The receiver compartment was then filled with 0.02% sodium azide solution and the cell was then placed in a circulating water bath calibrated to maintain the skin surface temperature at 32±1° C. At predetermined intervals, the entire contents of the receiver compartment was collected for drug quantitation, and the receiver compartment was refilled with fresh receptor medium, taking care to eliminate any air bubbles at the skin/solution interface. The cumulative amount of drug permeated per unit area at any time t ($Q_t$, µg/cm²) was determined as follows:

$$Q_t = \sum_{n=0}^{t} (C_n * V)/A$$

where $C_n$ is the concentration (mg/ml) of drug in the receiver sample for the corresponding sample time, V is the volume of fluid in the receiver chamber (~6.3 cm³), and A is the diffusional area of the cell (0.64 cm²). The slope of the best fit line to the $Q_t$ vs. t plot gives the steady state flux ($J_{ss}$, µg/cm²/h); the intercept of this line on the time axis gives the lag time ($t_L$, h).

Three formulations (Table I, Formulations 1-3), with progressively increasing NEA loading (1.5-6% w/w) along with a control formulation were evaluated for in vitro skin flux as described above on the same donor skins. The purpose of the control formulation was to minimize inherent skin to skin variability and allow for better elucidation of trends in the results. The in vitro drug fluxes from the test formulations were normalized on an individual skin basis relative to the fluxes from the control formulation which was run simultaneously on the same donor skins in this and subsequent experiments. This normalization procedure significantly minimized inter skin variability and allowed for easy comparison of relative flux performance between formulations in this and subsequent experiments. The NEA fluxes obtained for the Formulations 1-3 and the control formulation are summarized in Table II. The normalized flux ratios are plotted in FIG. 1.

As can be seen from the data presented in FIG. 1, a 4 fold increase in the drug loading results in a proportional 4 fold increase in the flux. The normalized in vitro NEA fluxes therefore display linear and Fickian dependence on the drug concentration between 1.5-6% w/w loading in matrices made with the NVP containing TSR acrylic copolymer adhesive.

TABLE I

COMPOSITION OF FORMULATIONS EVALUATED

| Formulation ID | TSR Adhesive % w/w | NEA % w/w | E2 % w/w | ARLACEL 80 % w/w |
|---|---|---|---|---|
| Test Formulations | | | | |
| 1. Lot #040695-1 | 88.5 | 1.5 | 0.0 | 10.0 |
| 2. Lot #040695-2 | 87.0 | 3.0 | 0.0 | 10.0 |
| 3. Lot #040695-3 | 84.0 | 6.0 | 0.0 | 10.0 |
| Control Formulation | | | | |
| 4. Control #95Z007 NEA Control Formulation | 77.8 | 6.0 | 6.2 | 10.0 |

TABLE II

CUMULATIVE NEA PERMEATION IN 96 hr (Q96-µg/cm²/96 hr)

| Formulation ID | # of skins/cells | Q96* | Ratio⁺ |
|---|---|---|---|
| Test Formulations | | | |
| 1. Lot #040695-1 | 6/24 | 8.4 ± 2.5 | 0.27 ± 0.06 |
| 2. Lot #040695-2 | 6/24 | 17.3 ± 3.8 | 0.55 ± 0.10 |
| 3. Lot #040695-3 | 6/24 | 32.9 ± 8.9 | 1.00 ± 0.08 |

*Q96-Cumulative amount permeated from test formulation in 96 hr
⁺Skin flux normalized relative to Control formulation on an individual skin basis. Control = 32.0 ± 7.9

(B) Estradiol (E2) only matrices:

Matrix laminates containing estradiol (E2, Berlichem, Wayne, N.J.) were prepared as described above in Example 1 (A) except that E2 was used as the drug instead of NEA. Necessary amounts of E2 were pre-dissolved in iso-propyl alcohol (IPA) and added to the casting solution to yield various compositions as shown in Table III below (Formulations 5-7).

TABLE III

COMPOSITION OF FORMULATIONS EVALUATED

| Formulation ID | TSR Adhesive % w/w | NEA % w/w | E2 % w/w | ARLACEL 80 % w/w |
|---|---|---|---|---|
| Test Formulations | | | | |
| 5. Lot #040695-4 | 87.0 | 0.0 | 3.0 | 10.0 |
| 6. Lot #040695-8 | 83.8 | 0.0 | 6.2 | 10.0 |
| 7. Lot #040695-12 | 81.0 | 0.0 | 9.0 | 10.0 |
| Control Formulation | | | | |
| 8. Control #94Z003 E2 Control Formulation | 93.5* | 0.0 | 1.5 | 5.0 |

*Formulation made with DUROTAK 87-2070 Adhesive, National Starch and Chemical Company, Bridgewater, NJ These formulations were evaluated for in vitro skin flux along with an E2 control formulation (Formulation 8). The in vitro skin fluxes for the three test formulations and the control formulation on the same skins are presented in Table IV below. The normalized flux ratio are plotted in FIG. 2.

Figure 2:
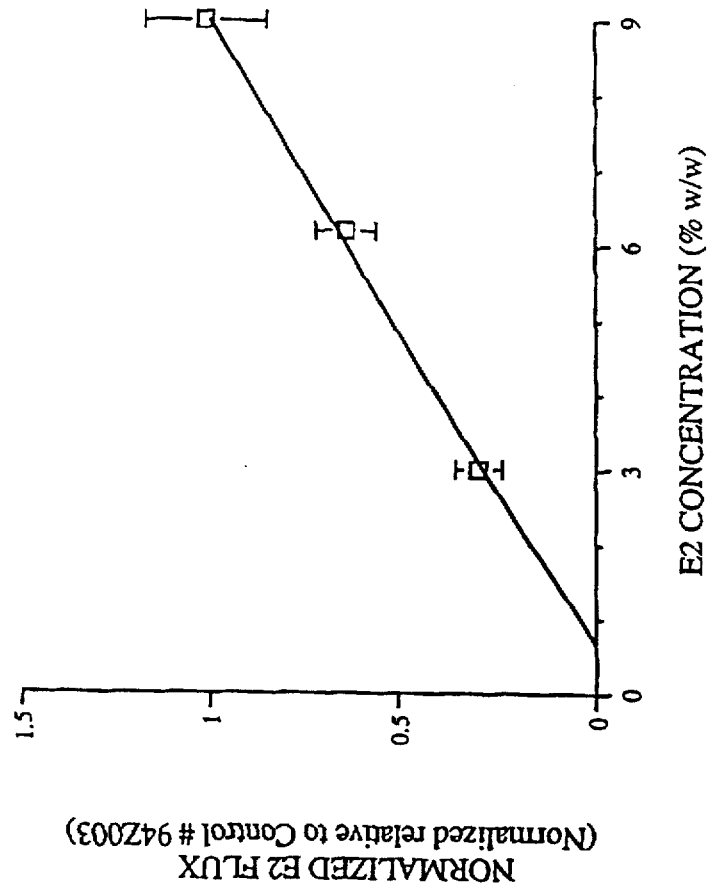
FIG. 2 is a graph showing normalized flux of estradiol (E2) as a function of the estradiol loading concentration from a NVP-containing matrix. The Y axis shows the normalized E2 flux relative to control #94Z003 (y=0.120x−0.080, $r^2$=0.997).

As can be seen from the data presented in FIG. 2, a 3 fold increase in the drug loading results in a proportional 3 fold increase in the flux. The normalized in vitro E2 fluxes therefore display linear and Fickian dependence on the drug concentration between 3–9% w/w loading in matrices made with the NVP containing TSR acrylic copolymer adhesive.

TABLE IV

CUMULATIVE E2 PERMEATION IN 96 hr (Q96-µg/cm²/96 hr)

| Formulation ID | # of skins/cells | Q96* | Ratio⁺ |
|---|---|---|---|
| Test Formulations | | | |
| 5. Lot #040695-4 | 6/24 | 6.1 ± 1.7 | 0.29 ± 0.06 |
| 6. Lot #040695-8 | 6/24 | 13.4 ± 4.0 | 0.64 ± 0.08 |
| 7. Lot #040695-12 | 6/24 | 20.9 ± 5.6 | 1.0 ± 0.16 |

*Q96-Cumulative amount permeated from test formulation in 96 hr
⁺Skin flux normalized relative to Control formulation on an individual skin basis. Control = 20.6 ± 4.4

(C) NEA/E2 coflux matrices:

Matrix laminates containing both E2 and NEA in combination were prepared as described above in Example 1 (A). Necessary amounts of E2 were pre-dissolved in isopropyl alcohol (IPA) and added to the casting solution along with NEA and sorbitan monooleate to yield various compositions as shown in Table V below (Formulations 9–17).

TABLE V

COMPOSITION OF FORMULATIONS EVALUATED

| Formulation ID | TSR Adhesive % w/w | NEA % w/w | E2 % w/w | ARLACEL 80 % w/w |
|---|---|---|---|---|
| Test Formulations | | | | |
| 9. Lot #040695-5 | 85.5 | 1.5 | 3.0 | 10.0 |
| 10. Lot #040695-6 | 84.0 | 3.0 | 3.0 | 10.0 |
| 11. Lot #040695-7 | 81.0 | 6.0 | 3.0 | 10.0 |
| 12. Lot #040695-9 | 82.3 | 1.5 | 6.2 | 10.0 |
| 13. Lot #040695-10 | 80.8 | 3.0 | 6.2 | 10.0 |
| 14. Lot #040695-11 | 77.8 | 6.0 | 6.2 | 10.0 |
| 15. Lot #040695-13 | 79.5 | 1.5 | 9.0 | 10.0 |
| 16. Lot #040695-14 | 78.0 | 3.0 | 9.0 | 10.0 |
| 17. Lot #040695-15 | 75.0 | 6.0 | 9.0 | 10.0 |
| Control Formulations | | | | |
| 4. Control #95Z007 NEA Control Formulation | 77.8 | 6.0 | 6.2 | 10.0 |
| 8. Control #94Z003 E2 Control Formulation | 93.5* | 0.0 | 1.5 | 5.0 |

Figure 3:
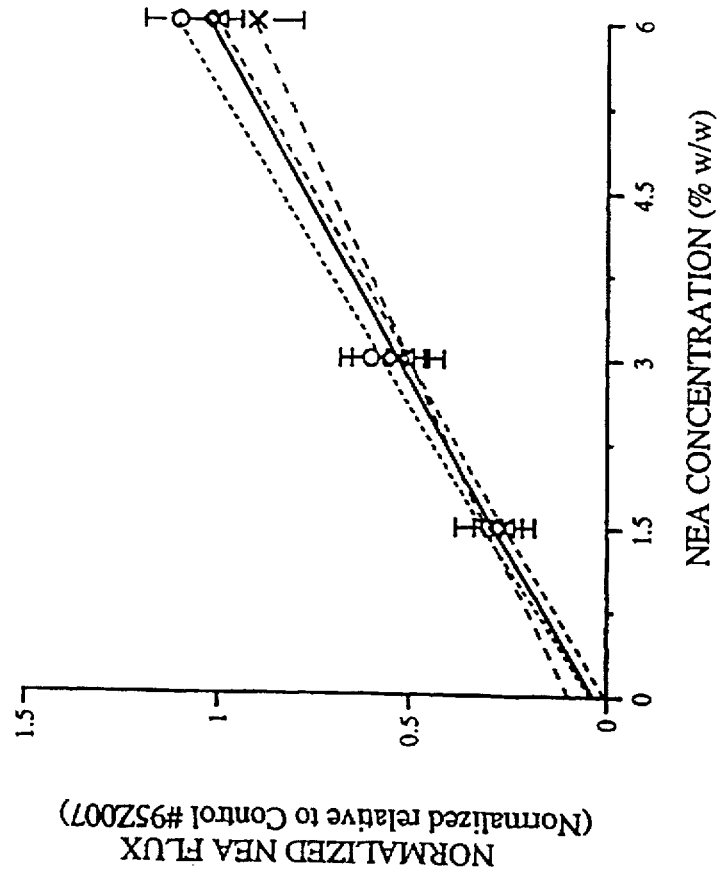
FIG. 3 is a graph of a series of curves showing the effects of different estradiol (E2) loading concentrations on the skin flux of NEA from a NVP-containing matrix. The Y axis shows the normalized NEA flux relative to control #95Z007. The figure legend for the graph is: ◇=variable NEA, no E2, y=0.165x+0.035, $r^2$=0.998; ○=variable NEA, 3% E2, y=0.178x+0.040, $r^2$=0.997; △=variable NEA, 6.2% E2, y=0.166x+0.005, $r^2$=1.000; x=variable NEA, 9% E2, y=0.136x+0.095, $r^2$=0.994.
Figure 4:
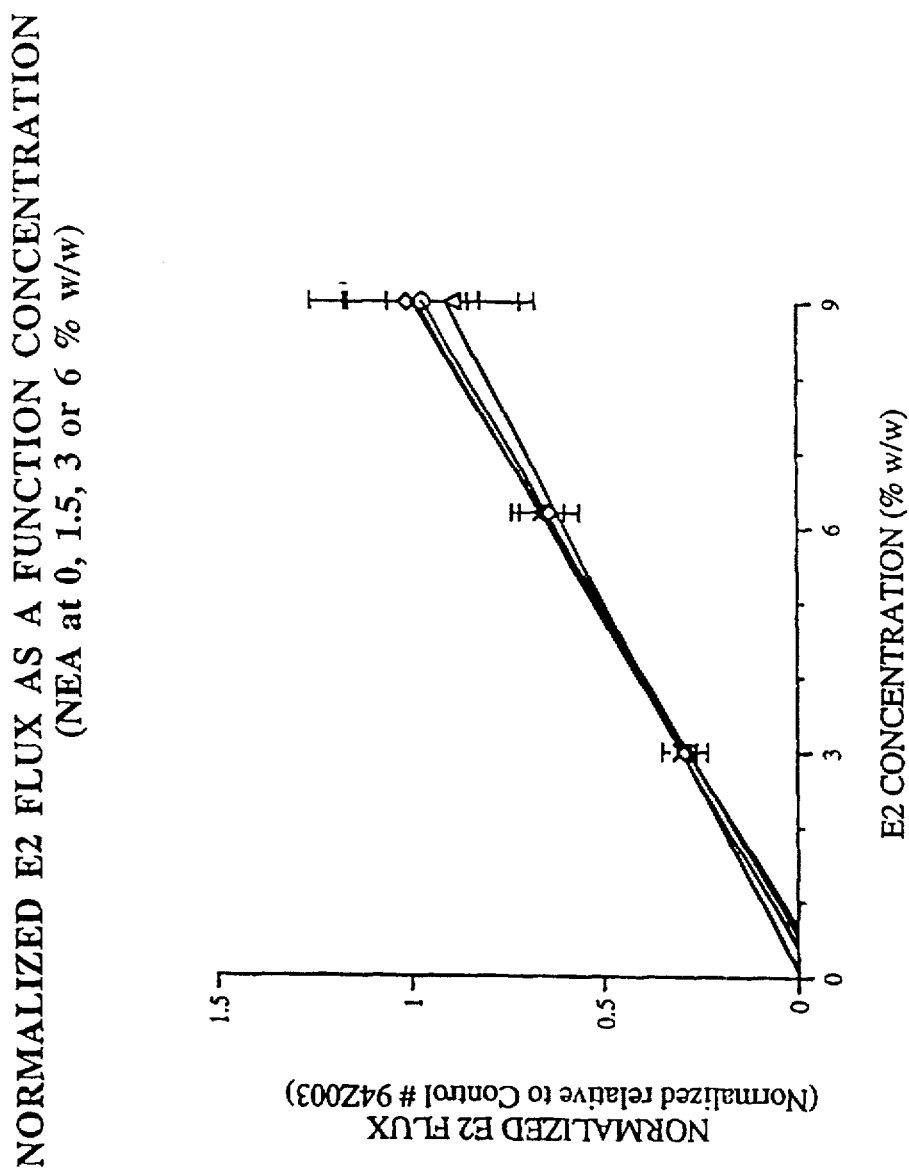
FIG. 4 is a graph of a series of curves showing the effects of different NEA concentrations on the skin flux of E2 from a NVP-containing matrix. The Y axis shows normalized E2 flux relative to control #94Z003. The figure legend for the graph is: ◇=variable E2, no NEA, y=0.120x−0.080, $r^2$=0.997; ○=variable E2, 1.5% NEA, y=0.115x−0.064, $r^2$=1.000; x=variable E2, 3% NEA, y=0.115x−0.047, $r^2$=1.000; △=variable E2, 6% NEA, y=0.102x−0.009, $r^2$=0.990.

*Formulation made with DUROTAK 87-2070 Adhesive, National Starch and Chemical Company, Bridgewater, NJ As can be seen from the data in FIG. 3, a 4 fold increase in the NEA loading results in a proportional 4 fold increase in the flux of NEA. Similarly, a 3 fold increase in E2 loading results in a proportional 3 fold increase in E2 flux (FIG. 4). The normalized in vitro NEA and E2 fluxes therefore display linear and Fickian dependence on the drug concentration in the presence of each other in matrices made with the NVP containing TSR acrylic copolymer adhesive over the range of drug loadings investigated (0–6% NEA loading and 0–9% E2 loading).

TABLE VI

CUMULATIVE NEA & E2 PERMEATION IN 96 hr (Q96 - µg/cm²/96 hr)

| | | Test Formulations | | | | | |
|---|---|---|---|---|---|---|---|
| | | NEA data | | | E2 data | | |
| Formulation ID | # of skins/cells | Q96* | Q96 (Control)ˣ | Ratio | Q96* | Q96 (Control)ˣ | Ratio⁺ |
| 9. Lot #040695-5 | 7/28 | 7.7 ± 3.6 | 25.7 ± 11.0 | 0.29 ± 0.02 | 5.4 ± 2.4 | 18.7 ± 6.8 | 0.28 ± 0.03 |
| 10. Lot #040695-6 | 7/28 | 15.4 ± 6.3 | 25.7 ± 11.0 | 0.6 ± 0.03 | 5.7 ± 2.3 | 18.7 ± 6.8 | 0.30 ± 0.02 |
| 11. Lot #040695-7 | 7/28 | 27.6 ± 11.0 | 25.7 ± 11.0 | 1.1 ± 0.09 | 5.4 ± 2.5 | 18.7 ± 6.8 | 0.28 ± 0.04 |
| 12. Lot #040695-9 | 5/20 | 7.0 ± 1.9 | 27.8 ± 7.7 | 0.25 ± 0.03 | 10.1 ± 2.7 | 15.8 ± 5.5 | 0.65 ± 1.10 |
| 13. Lot #040695-10 | 5/20 | 14.2 ± 4.2 | 27.8 ± 7.7 | 0.51 ± 0.05 | 10.4 ± 3.5 | 15.8 ± 5.5 | 0.66 ± 0.03 |
| 14. Lot #040695-11 | 5/20 | 27.8 ± 7.7 | 27.8 ± 7.7 | 1.0 ± 0.0 | 10.2 ± 3.0 | 15.8 ± 5.5 | 0.66 ± 0.06 |
| 15. Lot #040695-13 | 6/24 | 8.9 ± 2.6 | 37.4 ± 22.3 | 0.28 ± 0.10 | 20.3 ± 7.5 | 24.7 ± 16.3 | 0.97 ± 0.30 |
| 16. Lot #040695-14 | 6/24 | 18.3 ± 8.7 | 37.4 ± 22.3 | 0.53 ± 0.12 | 23.0 ± 13.5 | 24.7 ± 16.3 | 0.99 ± 0.17 |
| 17. Lot #040695-15 | 6/24 | 32.4 ± 18.0 | 37.4 ± 22.3 | 0.90 ± 0.12 | 21.3 ± 13.2 | 24.7 ± 16.3 | 0.89 ± 0.17 |

*Q96—Cumulative amount permeated from test formulation in 96 hr
ˣQ96 (Control)—Cumulative amount permeated from Control formulation in 96 hr on same skins as the test formulations
⁺Skin flux normalized relative to Control formulation on an individual skin basis These formulations were evaluated for in vitro skin flux along with NEA and E2 control formulations (Formulations 4 and 8 respectively) described above in Examples 1(A) and 1(B) respectively. The in vitro skin fluxes for the test formulations and the control formulations on the same skins are presented in Table VI. The normalized NEA and E2 flux ratio are plotted in FIGS. 3 and 4 respectively.

The slope of each of the three linear regression lines (normalized data for NEA fluxes in the presence of E2, FIG. 3) was compared statistically to the slope of the regression line for the NEA formulations without E2 using a Student's t-test. The results indicated that there was no statistically significant difference (p>0.10) in slopes between each of the three linear regression lines (for NEA formulations containing E2) relative to the slope of the regression line for the NEA formulations without E2. This confirms that the presence of E2 in the matrix does not affect the flux of NEA in systems made with the NVP containing TSR acrylic copolymer adhesive.

The slope of each of the three linear regression lines (normalized data for E2 fluxes in the presence of NEA, FIG. 4) was compared statistically to the slope of the regression line for the E2 formulations without NEA using a Student's t-test. The results indicated that there was no statistically significant difference (p>0.10) in slopes between each of the three linear regression lines (for E2 formulations containing NEA) relative to the slope of the regression line for the E2 formulations without NEA. This confirms that the presence of NEA in the matrix does not affect the flux of E2 in systems made with the NVP containing TSR acrylic copolymer adhesive.

The above data clearly shows that in systems prepared with the NVP containing acrylic copolymer adhesive, TSR, over the range of drug loadings investigated (0–6% NEA loading and 0–9% E2 loading), the flux of each steroid depends only on its concentration and is not affected by the presence of the other steroid.

Example 2

(A) NEA only matrices:

NEA only matrices were prepared as described in Example 1(A) except that the adhesive used was DURO-TAK 87-2516 (an acrylic copolymer adhesive containing EHA, vinyl acetate and hydroxyethyl acrylate, National Starch and Chemical Co, Bridgewater, N.J.). This adhesive does not contain N-vinyl-2-pyrrolidone. Necessary amounts of NEA and sorbitan monooleate were dissolved in the adhesive solution to yield various final compositions as shown in Table VII below (Formulations 1–4).

TABLE VII

COMPOSITION OF FORMULATIONS EVALUATED

| Formulation ID | DUROTAK 87-2516 adhesive % w/w | NEA % w/w | E2 % w/w | ARLACEL 80 % w/w |
|---|---|---|---|---|
| Test Formulations | | | | |
| 1. Lot #013096-1 | 88.0 | 2.0 | 0.0 | 10.0 |
| 2. Lot #013096-2 | 86.0 | 4.0 | 0.0 | 10.0 |
| 3. Lot #013096-3 | 84.0 | 6.0 | 0.0 | 10.0 |
| 4. Lot #013096-4 | 82.0 | 8.0 | 0.0 | 10.0 |
| Control Formulation | | | | |
| 5. Control #95Z098 NEA/E2 Control Formulation | 77.6 | 6.0 | 6.4 | 10.0 |

*TSR adhesive, Sekisui Chemical Co., Osaka Japan

These formulations were evaluated for in vitro skin flux along with a control formulation (Formulation 5). The in vitro skin fluxes for the three test formulations and the control formulation on the same skins are presented in Table VIII below. The normalized flux ratios are plotted in FIG. 5.

Figure 5:
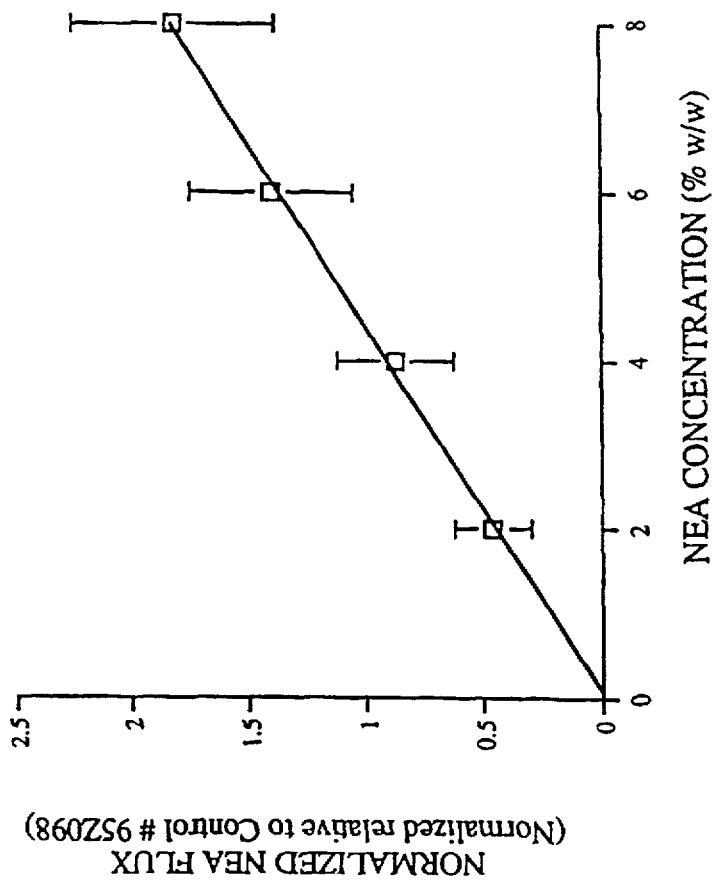
FIG. 5 is a graph showing normalized NEA flux as a function of the NEA loading concentration from matrices that do not contain NVP. The Y axis shows the normalized NEA flux relative to control #95Z098. The figure legend for the graph is: □=variable NEA, no E2, y=0.231x−0.015, $r^2$=0.997.

As can be seen from the data presented in FIG. 5, a 4 fold increase in the drug loading results in a proportional 4 fold increase in the flux. The normalized in vitro NEA fluxes therefore display linear and Fickian dependence on the drug concentration between 2–8% w/w loading in matrices made with DUROTAK 87-2516 adhesive.

TABLE VIII

CUMULATIVE NEA PERMEATION IN 24 hr (Q24-µg/cm$^2$/24 hr)

| Formulation ID | # of skins/cells | Q24* | Ratio+ |
|---|---|---|---|
| Test Formulations | | | |
| 1. Lot #013096-1 | 3/12 | 1.8 ± 0.7 | 0.5 ± 0.2 |
| 2. Lot #013096-2 | 3/12 | 3.5 ± 1.1 | 0.9 ± 0.3 |
| 3. Lot #013096-3 | 3/12 | 5.4 ± 0.7 | 1.4 ± 0.4 |
| 4. Lot #013096-4 | 3/12 | 8.6 ± 4.7 | 2.3 ± 1.8 |

*Q24-Cumulative amount permeated from test formation in 24 hr
+Skin flux normalized relative to Control formulation on an individual skin basis. Control = 4.1 ± 1.3

(B) E2 only matrices:

Matrix laminates containing E2 were prepared as described above in Example 1(A) except that E2 was used as the drug instead of NEA and DUROTAK 87-2516 was used as the adhesive instead of TSR. Necessary amounts of E2 were pre-dissolved in IPA and added to the casting solution to yield various compositions as shown in Table IX below (Formulations 6–8).

TABLE IX

COMPOSITION OF FORMULATIONS EVALUATED

| Formulation ID | DUROTAK 87-2516 adhesive % w/w | NEA % w/w | E2 % w/w | ARLACEL 80 % w/w |
|---|---|---|---|---|
| Test Formulations | | | | |
| 6. Lot #013096-5 | 89.0 | 0.0 | 1.0 | 10.0 |
| 7. Lot #013096-10 | 88.0 | 0.0 | 2.0 | 10.0 |
| 8. Lot #013096-15 | 86.0 | 0.0 | 4.0 | 10.0 |
| Control Formulation | | | | |
| 5. Control #95Z098 NEA/E2 Control Formulation | 77.6* | 6.0 | 6.4 | 10.0 |

*TSR adhesive, Sekisui Chemical Co., Osaka, Japan

These formulations were evaluated for in vitro skin flux along with a E2 control formulation (Formulation 5). The in vitro skin fluxes for the three test formulations and the control formulations on the same skins are presented in Table X. The normalized flux ratios are plotted in FIG. 6.

Figure 6:
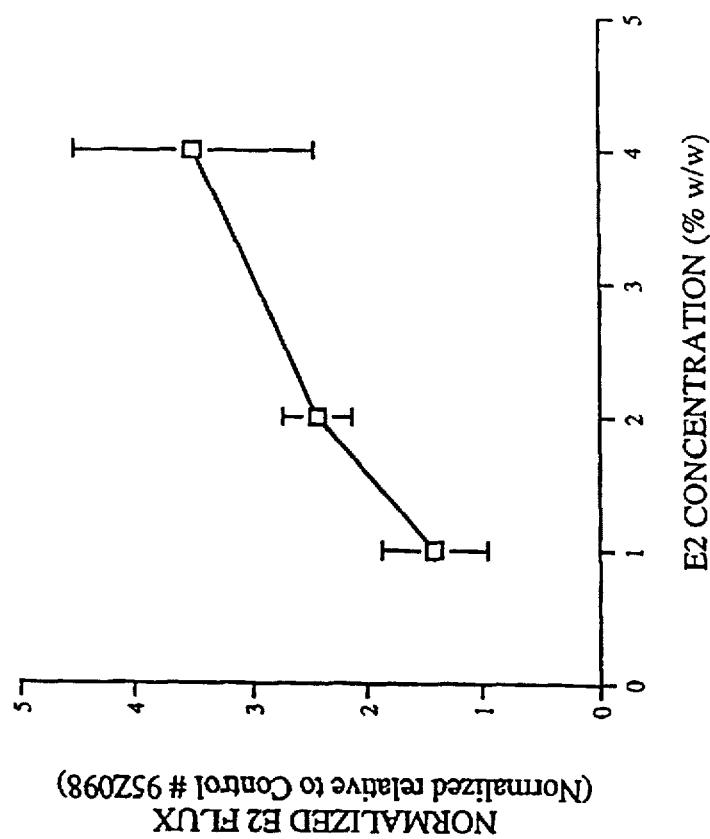
FIG. 6 is a graph showing normalized E2 flux as a function of the E2 loading concentration from matrices that do not contain NVP. The Y axis is the normalized E2 flux relative to control #95Z098 (□=variable E2, no NEA).

As can be seen from the data presented in FIG. 6, the normalized in vitro E2 fluxes increase linearly with drug concentration between 1–4% w/w loading in matrices made with DUROTAK 87-2516 adhesive.

TABLE X

CUMULATIVE E2 PERMEATION IN 24 hr (Q24-µg/cm$^2$/24 hr)

| Formulation ID | # of skins/cells | Q24* | Ratio+ |
|---|---|---|---|
| Test Formulations | | | |
| 6. Lot #013096-5 | 3/12 | 3.5 ± 1.1 | 1.4 ± 0.5 |

TABLE X-continued

CUMULATIVE E2 PERMEATION IN 24 hr (Q24-µg/cm$^2$/24 hr)

| Formulation ID | # of skins/cells | Q24* | Ratio+ |
|---|---|---|---|
| 7. Lot #013096-10 | 3/12 | 6.2 ± 1.1 | 2.4 ± 0.3 |
| 8. Lot #013096-15 | 3/12 | 9.0 ± 3.0 | 3.5 ± 1.0 |

*Q24-Cumulative amount permeated from test formulation in 24 hr
+Skin flux normalized relative to Control formulation on an individual skin basis. Control = 2.5 ± 0.6

(C) NEA/E2 coflux matrices:

Matrix laminates containing both E2 and NEA in combination were prepared as described above in Example 1 (A) except that the adhesive used was DUROTAK 87-2516 instead of TSR. Necessary amounts of E2 was pre-dissolved in IPA and added to the casting solution along with NEA and sorbitan monooleate to yield various compositions as shown in Table XI below (Formulations 9-20).

TABLE XI

COMPOSITION OF FORMULATIONS EVALUATED

| Formulation ID | DUROTAK 87-2516 Adhesive % w/w | NEA % w/w | E2 % w/w | ARLACEL 80 % w/w |
|---|---|---|---|---|
| Test Formulations | | | | |
| 9. Lot #013096-6 | 87.0 | 2.0 | 1.0 | 10.0 |
| 10. Lot #013096-7 | 85.0 | 4.0 | 1.0 | 10.0 |
| 11. Lot #013096-8 | 83.0 | 6.0 | 1.0 | 10.0 |
| 12. Lot #013096-9 | 81.0 | 8.0 | 1.0 | 10.0 |
| 13. Lot #013096-11 | 86.0 | 2.0 | 2.0 | 10.0 |
| 14. Lot #013096-12 | 84.0 | 4.0 | 2.0 | 10.0 |
| 15. Lot #013096-13 | 82.0 | 6.0 | 2.0 | 10.0 |
| 16. Lot #013096-14 | 80.0 | 8.0 | 2.0 | 10.0 |
| 17. Lot #013096-16 | 84.0 | 2.0 | 4.0 | 10.0 |
| 18. Lot #013096-17 | 82.0 | 4.0 | 4.0 | 10.0 |
| 19. Lot #013096-18 | 80.0 | 6.0 | 4.0 | 10.0 |
| 20. Lot #013096-19 Control Formulation | 78.0 | 8.0 | 4.0 | 10.0 |
| 5. Control #95Z098 NEA/E2 Control Formulation | 77.6* | 6.0 | 6.4 | 10.0 |

*TSR Adhesive, Sekisui Chemical Co., Osaka, Japan.

These formulations were evaluated for in vitro skin flux along with a control formulation (Formulation 5) described above in Examples 3(A) and 3(B). The in vitro skin fluxes for the test formulations and the control formulations on the same skins are presented in Table XII. The normalized NEA and E2 flux ratios are plotted in FIGS. 7 and 8 respectively.

Figure 7:
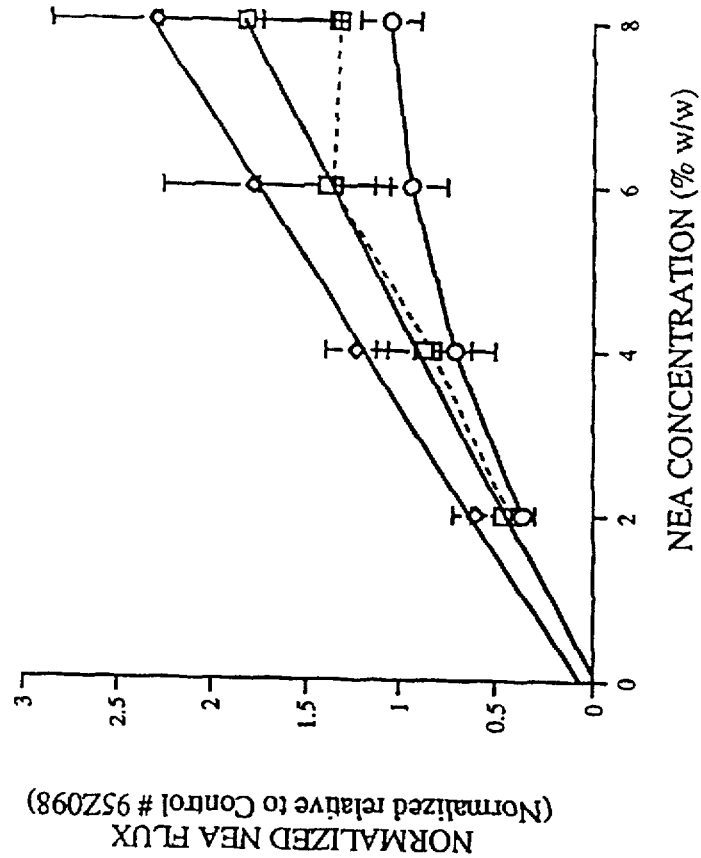
FIG. 7 is a series of curves showing the effects of different E2 loading concentrations on the skin flux of NEA from matrices that do not contain NVP. The Y axis shows the normalized NEA flux relative to control #95Z098. The figure legend for the graph is: □=variable NEA, no E2, y=0.231x−0.015, $r^2$=0.997; ◇=variable NEA, 1% E2, y=0.281x+0.070, $r^2$=0.998; □=variable NEA, 2% E2, ○=variable NEA, 4% E2.
Figure 8:
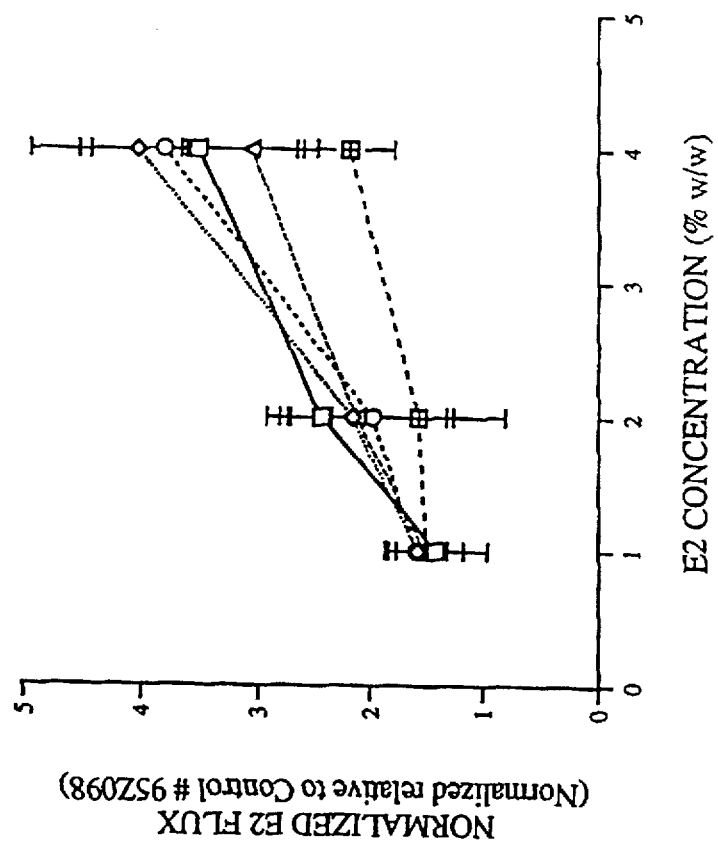
FIG. 8 is a series of curves showing the effects of different NEA loading concentrations on the skin flux of E2 from matrices that do not contain NVP. The Y axis shows the normalized E2 flux relative to control #95Z098. The figure legend for the graph is: □=variable E2, no NEA, ◇=variable E2, 2% NEA, ○=variable E2, 4% NEA, △=variable E2, 6% NEA and □=variable E2, 8% NEA.

As can be seen from the data in FIG. 7, a 4 fold increase in the NEA loading did not result in a proportional 4 fold increase in the flux of NEA. Similarly, a 4 fold increase in E2 loading did not result in a proportional 4 fold increase in E2 flux (FIG. 8). The normalized in vitro NEA and E2 fluxes therefore do not display linear and Fickian dependence on the steroid concentration in the presence of each other in matrices made with DUROTAK 87-2516 adhesive over the range of drug loadings investigated (0–8% NEA loading and 0–4% E2 loading).

TABLE XII

CUMULATIVE NEA & E2 PERMEATION IN 24 hr (Q24 - µg/cm$^2$/24 hr)

| | | Test Formulations | | | | | |
|---|---|---|---|---|---|---|---|
| | | NEA data | | | E2 data | | |
| Formulation ID | # of skins/cells | Q24* | Q24 (Control)ˣ | Ratio | Q24* | Q24 (Control)ˣ | Ratio+ |
| 9. Lot #013096-6 | 3/12 | 4.6 ± 1.3 | 7.6 ± 2.2 | 0.6 ± 0.1 | 5.3 ± 1.5 | 3.3 ± 1.0 | 1.6 ± 0.3 |
| 10. Lot #013096-7 | 3/12 | 9.4 ± 2.1 | 7.6 ± 2.2 | 1.2 ± 0.2 | 5.3 ± 1.2 | 3.3 ± 1.0 | 1.6 ± 0.2 |
| 11. Lot #013096-8 | 3/12 | 13.8 ± 4.8 | 7.6 ± 2.2 | 1.8 ± 0.5 | 5.1 ± 1.7 | 3.3 ± 1.0 | 1.5 ± 0.3 |
| 12. Lot #013096-9 | 3/12 | 17.5 ± 5.6 | 7.6 ± 2.2 | 2.3 ± 0.6 | 5.1 ± 1.7 | 3.3 ± 1.0 | 1.5 ± 0.3 |
| 13. Lot #013096-11 | 3/12 | 2.5 ± 0.5 | 6.1 ± 2.6 | 0.4 ± 0.1 | 5.9 ± 1.3 | 2.8 ± 1.2 | 2.2 ± 0.6 |
| 14. Lot #013096-12 | 3/12 | 4.8 ± 1.2 | 6.1 ± 2.6 | 0.8 ± 0.3 | 5.3 ± 1.4 | 2.8 ± 1.2 | 2.0 ± 0.7 |
| 15. Lot #013096-13 | 3/12 | 7.7 ± 1.8 | 6.1 ± 2.6 | 1.4 ± 0.5 | 5.5 ± 1.3 | 2.8 ± 1.2 | 2.1 ± 0.8 |
| 16. Lot #013096-14 | 3/12 | 7.8 ± 2.7 | 6.1 ± 2.6 | 1.3 ± 0.6 | 4.2 ± 1.6 | 2.8 ± 1.2 | 1.6 ± 0.8 |
| 17. Lot #013096-16 | 3/12 | 2.8 ± 0.7 | 8.1 ± 2.4 | 0.4 ± 0.04 | 12.8 ± 2.7 | 3.2 ± 0.8 | 4.0 ± 0.4 |
| 18. Lot #013096-17 | 3/12 | 5.6 ± 1.5 | 8.1 ± 2.4 | 0.7 ± 0.2 | 11.8 ± 3.0 | 3.2 ± 0.8 | 3.8 ± 1.2 |
| 19. Lot #013096-18 | 3/12 | 7.4 ± 1.5 | 8.1 ± 2.4 | 0.9 ± 0.2 | 9.6 ± 1.9 | 3.2 ± 0.8 | 3.1 ± 0.6 |
| 20. Lot #013096-19 | 3/12 | 8.2 ± 2.2 | 8.1 ± 2.4 | 1.1 ± 0.2 | 6.9 ± 1.4 | 3.2 ± 0.8 | 2.2 ± 0.4 |

*Q24—Cumulative amount permeated from test formulation in 24 hr
ˣQ24 (Control)—Cumulative amount permeated from Control formulation in 24 hr on same skins as the test formulations
+Skin flux normalized relative to Control formulation on an individual skin basis The above data clearly shows that in vitro E2 and NEA fluxes are influenced by the presence of each other, do not follow Fickian laws of diffusion, and are not proportional to the steroid concentration in the matrix laminates made with DUROTAK 87-2516 adhesive, over the range of steroid concentrations investigated (0–8% NEA loading and 0–4% E2 loading). The independent flux of the two steroids in the presence of each other and proportionality in skin flux as a function of steroid in the matrix is apparently unique to NVP containing acrylic copolymer adhesive.

Example 3

(A) Testosterone (TS) only matrices:

Testosterone (TS, Upjohn Company, Kalamazoo, Mich.) only matrices were prepared as described in Example 1 (A) except that the steroid used was TS instead of NEA. Necessary amounts of TS were pre-dissolved in IPA and added to the casting solution to yield various compositions as shown in Table XIII below (Formulations 1–3).

TABLE XIII

COMPOSITION OF FORMULATIONS EVALUATED

| Formulation ID | TSR Adhesive % w/w | TS % w/w | E2 % w/w | ARLACEL 80 % w/w |
|---|---|---|---|---|
| Test Formulations | | | | |
| 1. Lot #012496-1 | 87.5 | 2.5 | 0.0 | 10.0 |
| 2. Lot #012496-2 | 86.25 | 3.75 | 0.0 | 10.0 |
| 3. Lot #012496-3 | 85.0 | 5.0 | 0.0 | 10.0 |
| Control Formulation | | | | |
| 4. Control #95Z082 TS Control Formulation | 75.75 | 3.75 | 10.5 | 10.0 |

These formulations were evaluated for in vitro skin flux using a formulation containing TS as a control (Formulation 4). The in vitro skin fluxes for the three test formulations and the control formulations on the same skins are presented in Table XIV. The normalized flux ratios are plotted in FIG. 9.

Figure 9:
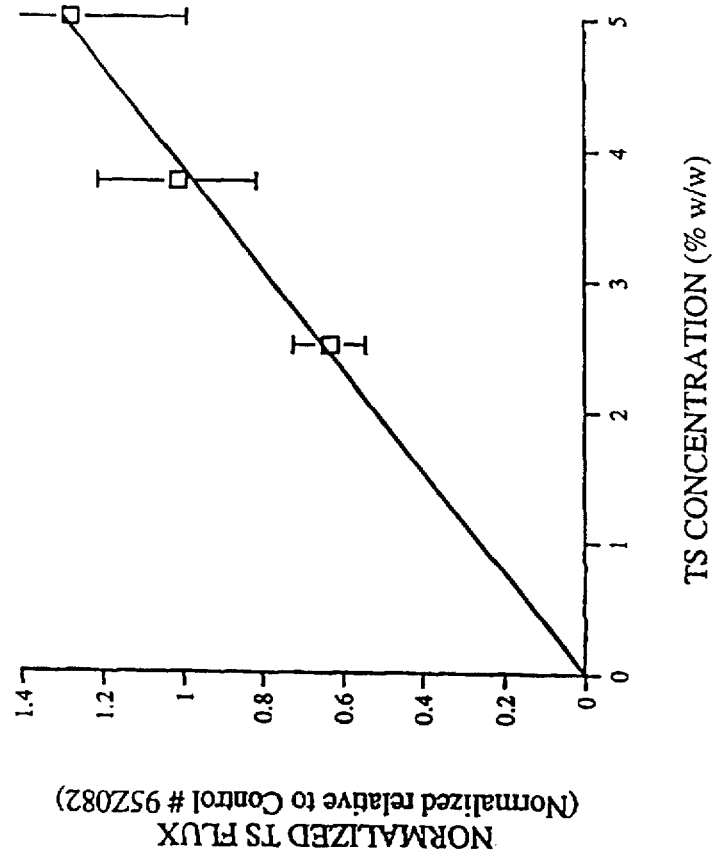
FIG. 9 is a graph showing normalized flux of testosterone (TS) as a function of the TS loading concentration from a NVP-containing matrix. The Y axis shows the normalized TS flux relative to control #95Z082. The figure legend for the graph is: □=variable TS, no E2, y=0.260x−0.002, $r^2$=0.991.

As can be seen from the data presented in FIG. 9, a 2 fold increase in the drug loading results in a proportional 2 fold increase in the flux. The normalized in vitro TS fluxes therefore display linear and Fickian dependence on the steroid concentration between 2.5–5% w/w loading in matrices made with TSR adhesive.

TABLE XIV

CUMULATIVE TS PERMEATION IN 24 hr (Q24-µg/cm²/24 hr)

| Formulation ID | # of skins/cells | Q24* | Ratio⁺ |
|---|---|---|---|
| Test Formulations | | | |
| 1. Lot #012496-1 | 3/12 | 15.6 ± 6.6 | 0.63 ± 0.09 |
| 2. Lot #012496-2 | 3/12 | 25.7 ± 13.4 | 1.01 ± 0.20 |
| 3. Lot #012496-3 | 3/12 | 31.8 ± 15.3 | 1.28 ± 0.29 |

*Q24-Cumulative amount permeated from test formulation in 24 hr
⁺Skin flux normalized relative to Control formulation on an individual skin basis. Control = 25.8 ± 10.5

(B) E2 only matrices:

Matrix laminates containing E2 were prepared as described above in Example 1 (A) except that E2 was used as the drug instead of NEA. Necessary amounts of E2 were pre-dissolved in IPA and added to the casting solution to yield various compositions as shown in Table XV below (Formulations 5–7).

These formulations were evaluated for in vitro skin flux along with a E2 control formulation (Formulation 8). The in vitro skin fluxes for the three test formulations and the control formulation on the same skins are presented in Table XVI. The normalized flux ratio's are plotted in FIG. 10.

Figure 10:
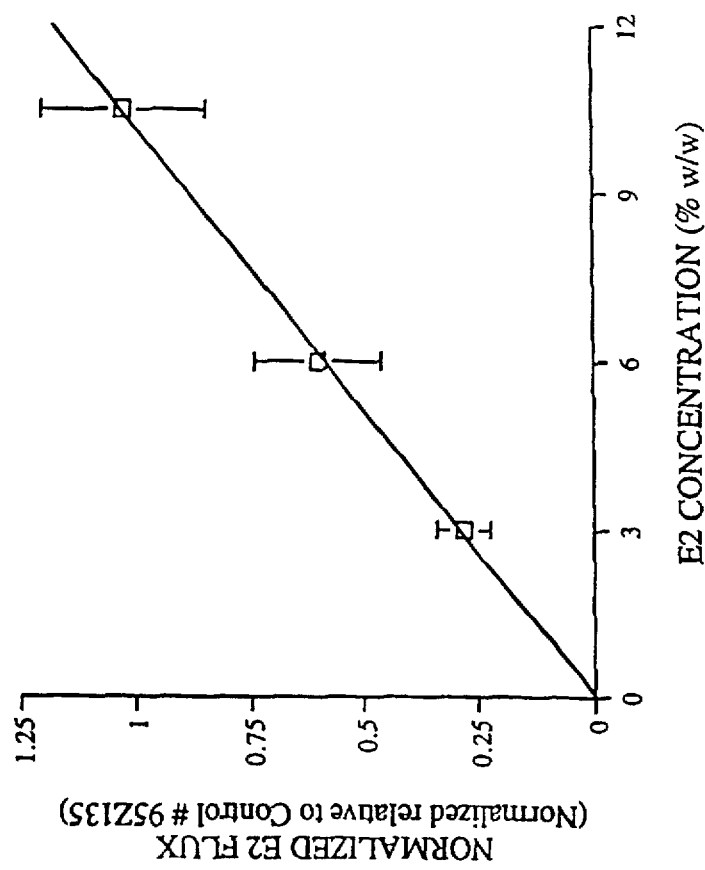
FIG. 10 is a graph showing normalized E2 flux as a function of the E2 loading concentration from a NVP-containing matrix. The Y axis shows the normalized E2 flux relative to control #95Z135. The figure legend for the graph is: □=variable E2, no TS, y=0.098x+0.005, $r^2$=0.999.

As can be seen from the data presented in FIG. 10, a 3.5 fold increase in the steroid concentration results in a proportional 3.5 fold increase in the flux. The normalized in vitro E2 fluxes therefore display linear and Fickian dependence on the steroid concentration between 3–10.5% w/w loading in matrices made with TSR adhesive.

TABLE XV

COMPOSITION OF FORMULATIONS EVALUATED

| Formulation ID | TSR Adhesive % w/w | TS % w/w | E2 % w/w | ARLACEL 80 % w/w |
|---|---|---|---|---|
| Test Formulations | | | | |
| 5. Lot #012496-4 | 87.0 | 0.0 | 3.0 | 10.0 |
| 6. Lot #012496-8 | 84.0 | 0.0 | 6.0 | 10.0 |
| 7. Lot #012496-12 | 79.5 | 0.0 | 10.5 | 10.0 |
| Control Formulation | | | | |
| 8. Control #95Z135 E2 Control Formulation | 93.5* | 0.0 | 1.5 | 5.0 |

*Formulation made with DUROTAK 87-2070 Adhesive, National Starch and Chemical Company, Bridgewater, NJ

TABLE XVI

CUMULATIVE E2 PERMEATION IN 24 hr (Q24-µg/cm²/24 hr)

| Formulation ID | # of skins/cells | Q24* | Ratio⁺ |
|---|---|---|---|
| Test Formulations | | | |
| 5. Lot #012496-4 | 3/12 | 2.6 ± 0.7 | 0.28 ± 0.06 |
| 6. Lot #012496-8 | 3/12 | 5.4 ± 0.9 | 0.60 ± 0.14 |
| 7. Lot #012496-12 | 3/12 | 9.3 ± 1.6 | 1.02 ± 0.18 |

*Q24-Cumulative amount permeated from test formulation in 24 hr
⁺Skin flux normalized relative to Control formulation on an individual skin basis. Control = 11.3 ± 2.0

(C) TS/E2 coflux matrices:

Matrix laminates containing both E2 and TS in combination were prepared as described above in Example 1 (A). Necessary amounts of E2 and TS were pre-dissolved in iso-propyl alcohol (IPA) and added to the casting solution along with sorbitan monooleate to yield various compositions as shown in Table XVII below (Formulations 9–17).

TABLE XVII

COMPOSITION OF FORMULATIONS EVALUATED

| Formulation ID | TSR Adhesive % w/w | TS % w/w | E2 % w/w | ARLACEL 80 % w/w |
|---|---|---|---|---|
| Test Formulations | | | | |
| 9. Lot #012496-5 | 84.5 | 2.5 | 3.0 | 10.0 |
| 10. Lot #012496-6 | 83.25 | 3.75 | 3.0 | 10.0 |

TABLE XVII-continued

COMPOSITION OF FORMULATIONS EVALUATED

| Formulation ID | TSR Adhesive % w/w | TS % w/w | E2 % w/w | ARLACEL 80 % w/w |
|---|---|---|---|---|
| 11. Lot #012496-7 | 82.0 | 5.0 | 3.0 | 10.0 |
| 12. Lot #012496-9 | 81.5 | 2.5 | 6.0 | 10.0 |
| 13. Lot #012496-10 | 80.25 | 3.75 | 6.0 | 10.0 |
| 14. Lot #012496-11 | 79.0 | 5.0 | 6.0 | 10.0 |
| 15. Lot #012496-13 | 77.0 | 2.5 | 10.5 | 10.0 |
| 16. Lot #012496-14 | 75.75 | 3.75 | 10.5 | 10.0 |
| 17. Lot #012496-15 | 74.5 | 5.0 | 10.5 | 10.0 |
| Control Formulations | | | | |
| 4. Control #95Z082 | 75.75 | 3.75 | 10.5 | 10.0 |
| TS Control Formulation | | | | |
| 8. Control #95Z135 | 93.5* | 0.0 | 1.5 | 5.0 |
| E2 Control Formulation | | | | |

*Formulation made with DUROTAK 87-2070 Adhesive, National Starch and Chemical Company, Bridgewater, NJ These formulations were evaluated for in vitro skin flux along with TS and E2 control formulations (Formulations 4 and 8 respectively) described above in Examples 2(A) and 2(B) respectively. The in vitro skin fluxes for the test formulations and the control formulations on the same skins are presented in Table XVIII below. The normalized TS and E2 flux ratios are plotted in FIGS. 11 and 12 respectively.

Figure 11:
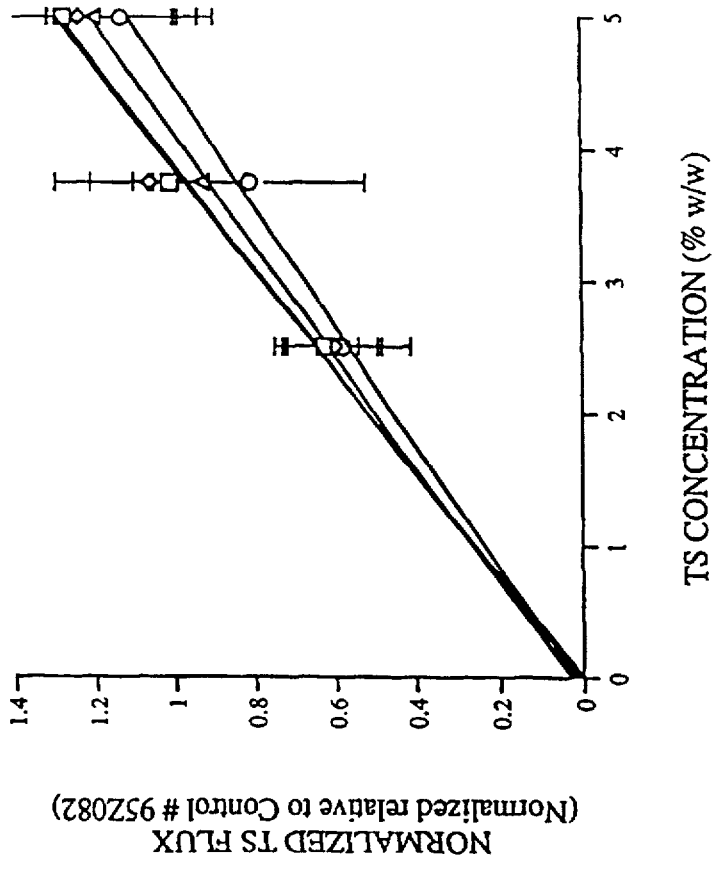
FIG. 11 is a series of curves showing the effects of different E2 loading concentrations on the skin flux of TS from a NVP-containing matrix. The Y axis shows the normalized TS flux relative to control #95Z082. The figure legend for the graph is: □=variable TS, no E2, y=0.260x−0.002, $r^2$=0.991; ◊=variable TS, 3% E2, y=0.256x+0.007, $r^2$=0.940; ○=variable TS, 6% E2, y=0.220x+0.0 15, $r^2$=0.991; ∆=variable TS, 10.5% E2, y=0.236x+0.028, $r^2$=0.998.
Figure 12:
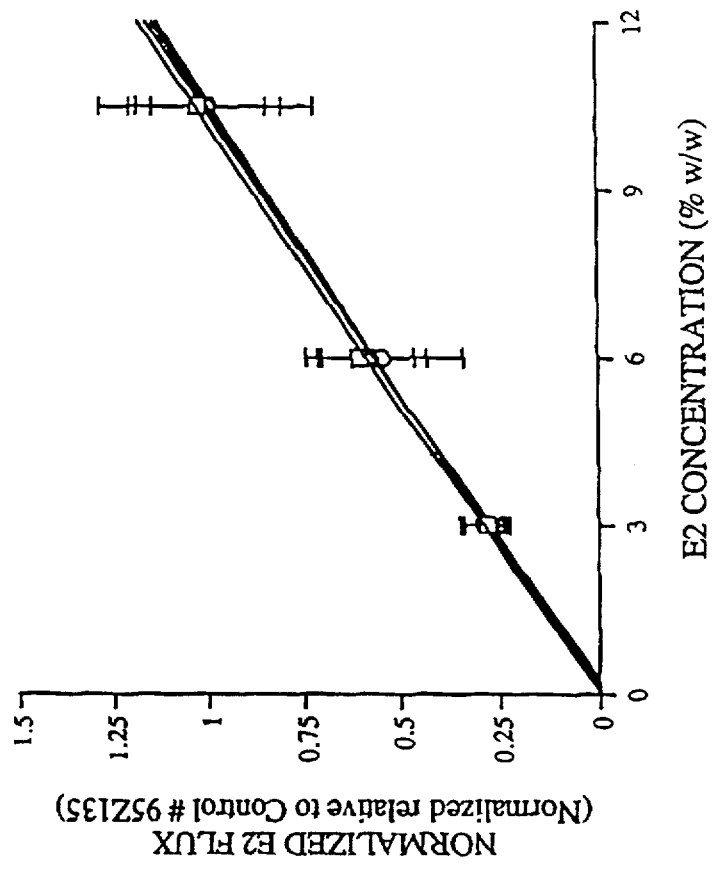
FIG. 12 is a series of curves showing the effects of different TS loading concentrations on the skin flux of E2 from NVP-containing matrices. The Y axis shows normalized E2 flux relative to control #95Z135. The figure legend for the graph is: □=variable E2, no TS, y=0.098x−0.005, $r^2$=0.999; ◊=variable E2, 2.5% TS, y=0.096x−0.013, $r^2$=1.000; ○=variable E2, 3.75% TS, y=0.094x−0.003, $r^2$=0.998; ∆=variable E2, 5% TS, y=0.098x−0.025, $r^2$=0.999.

As can be seen from the data in FIG. 11, a 2 fold increase in the TS loading results in a proportional 2 fold increase in the flux of TS. Similarly, a 3.5 fold increase in E2 concentration results in a proportional 3.5 fold increase in E2 flux (FIG. 12). The normalized in vitro TS and E2 fluxes therefore display linear and Fickian dependence on the steroid concentration in the presence of each other in matrices made with the NVP containing TSR acrylic copolymer adhesive over the range of steroid concentrations investigated (0–5% TS and 0–10.5% E2).

The slope of each of the three linear regression lines (normalized data for TS fluxes in the presence of E2, FIG. 11) was compared statistically to the slope of the regression line for the TS formulations without E2 using a Student's t-test. The results indicated that there was no statistically significant difference (p>0.10) in slopes between each of the three linear regression lines (for TS formulations containing E2) relative to the slope of the regression line for the TS formulations without E2. This confirms that the presence of E2 in the matrix does not affect the flux of TS in systems made with the NVP containing TSR acrylic copolymer adhesive.

The slope of each of the three linear regression lines (normalized data for E2 fluxes in the presence of TS, FIG. 12) was compared statistically to the slope of the regression line for the E2 formulations without TS using a Student's t-test. The results indicated that there was no statistically significant difference (p>0.10) in slopes between each of the three linear regression lines (for E2 formulations containing TS) relative to the slope of the regression line for the E2 formulations without TS. This confirms that the presence of TS in the matrix does not affect the flux of E2 in systems made with the NVP containing TSR acrylic copolymer adhesive.

The above data clearly shows that over the range of steroid concentrations investigated (0–5% TS loading and 0–10.5% E2), in vitro E2 and TS fluxes are independent of each other, follow Fickian laws of diffusion, and are proportional to the steroid concentration in the matrix laminates made with the NVP containing acrylic copolymer adhesive, TSR. The independence in fluxes for the two steroids in the presence of each other and proportionality in in vitro skin flux as a function of steroid concentration in the matrix again appears to be unique to the NVP acrylic copolymer adhesive.

TABLE XVIII

CUMULATIVE TS & E2 PERMEATION IN 24 hr (Q24 - µg/cm$^2$/24 hr)

| | | Test Formulations | | | | | |
|---|---|---|---|---|---|---|---|
| | | TS data | | | E2 data | | |
| Formulation ID | # of skins/cells | Q24* | Q24 (Control)$^x$ | Ratio | Q24* | Q24 (Control)$^x$ | Ratio$^+$ |
| 9. Lot #012496-5 | 3/12 | 14.2 ± 6.1 | 23.0 ± 9.3 | 0.60 ± 0.1 | 1.4 ± 0.5 | 5.2 ± 1.8 | 0.27 ± 0.04 |
| 10. Lot #012496-6 | 3/12 | 24.2 ± 9.0 | 23.0 ± 9.3 | 1.06 ± 0.2 | 1.5 ± 0.5 | 5.2 ± 1.8 | 0.29 ± 0.06 |
| 11. Lot #012496-7 | 3/12 | 28.1 ± 9.5 | 23.0 ± 9.3 | 1.24 ± 0.2 | 1.4 ± 0.4 | 5.2 ± 1.8 | 0.26 ± 0.04 |
| 12. Lot #012496-9 | 3/10 | 13.2 ± 2.9 | 23.2 ± 8.4 | 0.58 ± 0.2 | 2.6 ± 0.5 | 4.7 ± 1.6 | 0.57 ± 0.14 |
| 13. Lot #012496-10 | 3/10 | 18.2 ± 4.5 | 23.2 ± 8.4 | 0.81 ± 0.3 | 2.4 ± 0.6 | 4.7 ± 1.6 | 0.54 ± 0.20 |
| 14. Lot #012496-11 | 3/11 | 26.3 ± 7.9 | 23.2 ± 8.4 | 1.13 ± 0.2 | 2.7 ± 0.7 | 4.7 ± 1.6 | 0.58 ± 0.12 |
| 15. Lot #012496-13 | 3/12 | 14.4 ± 7.8 | 22.5 ± 10.0 | 0.61 ± 0.1 | 6.2 ± 3.2 | 5.9 ± 2.4 | 0.99 ± 0.19 |
| 16. Lot #012496-14 | 3/12 | 21.4 ± 10.9 | 22.5 ± 10.0 | 0.93 ± 0.1 | 6.2 ± 3.1 | 5.9 ± 2.4 | 0.99 ± 0.15 |
| 17. Lot #012496-15 | 3/12 | 26.6 ± 10.6 | 22.5 ± 10.0 | 1.20 ± 0.3 | 6.0 ± 2.2 | 5.9 ± 2.4 | 1.0 ± 0.28 |

*Q24—Cumulative amount permeated from test formulation in 24 hr
$^x$Q24 (Control)—Cumulative amount permeated from Control formulation in 24 hr on same skins as the test formulations
$^+$Skin flux normalized relative to Control formulation on an individual skin basis

We claim:

1. A transdermal patch for administering estradiol and another steroid comprising:
   a) a backing layer; and
   b) a matrix layer comprising:
      (i) a pressure sensitive adhesive copolymer of N-vinyl-2-pyrrolidone-and 2-ethylhexyl acrylate;
      (ii) estradiol; and
      (iii) another sex steroid other than an estradiol or ester of an estradiol, wherein the flux of said sex steroid from the matrix layer is independent of the concentration of estradiol in the matrix layer and the flux of estradiol from the matrix layer is independent of the concentration of the other sex steroid in the matrix layer.

2. The transdermal patch of claim 1 wherein the 2-ethylhexyl acrylate constitutes 45 to 80 mol % of the copolymer and the N-vinyl-2-pyrrolidone constitutes 20 to 55 mol % of the copolymer.

3. The transdermal patch of claim 1 wherein the 2-ethylhexyl acrylate constitutes 55 to 70 mol % of the copolymer and the N-vinyl-2-pyrrolidone constitutes 30 to 45 mol % of the copolymer.

4. The transdermal patch of claim 1 wherein the concentration of estradiol in the matrix layer is about 1 to 20% by weight and the concentration of the other steroid is about 1 to 20%.

5. The transdermal patch of claim 1 wherein the other steroid is norethindrone acetate.

6. The transdermal patch of claim 1 wherein the other steroid is testosterone.

7. The transdermal patch of claim 5 wherein the concentration of estradiol in the matrix layer is 2 to 12% by weight, the concentration of norethindrone acetate in the matrix layer is 1 to 8% by weight.

8. The transdermal patch of claim 6 wherein the concentration of estradiol in the matrix layer is 2 to 12% by weight, the concentration of testosterone in the matrix layer is 1 to 8% by weight.

9. A method of providing hormone replacement therapy to a woman in need of said therapy comprising applying the patch of claim 1 to the skin of said woman.

* * * * *